United States Patent [19]

Pecaut et al.

[11] Patent Number: 5,514,807

[45] Date of Patent: May 7, 1996

[54] 5-AMINO-5-NITROPYRIDINIUM HALIDE CRYSTAL STRUCTURE

[75] Inventors: Jacques Pecaut, Avignon; Jean-Pierre Levy, Grenoble; René Masses, Crolles; Joseph Zyss, Sceaux; Rolland Hierle, Paris, all of France

[73] Assignee: France Telecom & Centre National de la Recherche Scientifique (CNRS), Paris, France

[21] Appl. No.: 223,059

[22] Filed: Apr. 6, 1994

[30] Foreign Application Priority Data

Apr. 7, 1993 [FR] France .................. 93 04116

[51] Int. Cl.⁶ ............................ C07D 213/90
[52] U.S. Cl. ............................ 546/307; 546/297
[58] Field of Search .................. 546/297, 307

[56] References Cited

U.S. PATENT DOCUMENTS 5,374,734  12/1994  Zyss et al. ............... 546/347

FOREIGN PATENT DOCUMENTS 0488869  11/1990  European Pat. Off. ......... 546/297

OTHER PUBLICATIONS

Vidakovic et al, J. Opt. Soc. Am. B/vol. 4, No. 6., Jun. 1987, pp. 998–1012.
Meredith, Nonlinear Optical Properties, pp. 27–56, 1983.
Zyss et al, J. Chem. Phys., vol. 74, No. 9, May 1, 1981, pp. 4800–4811.
Zyss et al, J. Chem. Phys., vol. 81, No. 91, Nov. 1, 1984, pp. 4160–4167.
Masse et al., Molecular Engineering, vol. 1, pp. 141–152, 1991.
Lipscomb et al, J. Chem. Phys., vol. 75, No. 3, Aug. 1, 1981, pp. 1509–1516.
Zyss et al, Chem. Physics., vol. 150, 1991, pp. 125–135.
Okaya et al, Acta Cryst., vol. 21, pp. 237–243. 1966.
Albertsson et al, Appl. Cryst., vol. 12, pp. 537–544, 1979.
Watanabe et al, J. Mater. Chem., vol. 3, No. 10, 1993, pp. 1053–1057.
Schnekenburger et al, Arch. Pahrm, vol. 316, No. 1, pp. 27–33, 1983.
Journal of the Chemical Society, Chemical Communications No. 23, 1989, pp. 1856–1851859, C. B. Aakeroy et al "A novel class of salts for harmonic generation".
Acta Crystallographica Section B: Structural Science, vol. B49, No. 2, 1 Apr. 1993, Copenhagen pp. 277–282 J. Pecaut; R. masse "Structure of Bis(2–amino–5–nitropyridinium) dichrmate . . . ".
Pecaut et al. J. Materials Chem., 1993, vol. 3, No. 10, pp. 999–1003.
de Bie et al., J. Org. Chem, 1985. vol. 50, pp. 484–487.

*Primary Examiner*—C. Warren Ivy
*Assistant Examiner*—Zinna N. Davis
*Attorney, Agent, or Firm*—Blakely, Sokoloff, Taylor & Zafman

[57] ABSTRACT

The present invention relates to new noncentrosymmetric crystal structures consisting of an optionally substituted 2-amino-5-nitropyridinium halide.

It also relates to a process for the preparation of these crystal structures. Finally, it relates to a device with an electro-optical effect comprising said crystal structure.

3 Claims, 2 Drawing Sheets

FIG_1

5-AMINO-5-NITROPYRIDINIUM HALIDE CRYSTAL STRUCTURE

FIELD OF THE INVENTION

The present invention relates to new crystal structures useable in nonlinear optics and in electro-optics. It relates more particularly to new crystal structures exhibiting quadratic nonlinear effects and a wide transparency range extending from the visible to the near infrared. Finally, it relates to a process for the preparation of these crystal structures and a device with an electro-optical effect comprising such a crystal structure.

As a result of its noncentrosymmetric structure, which gives it a quadratic nonlinear susceptibility tensor $\chi^2$, the crystal according to the invention can be used in any configuration of a mixture with three waves of "all-optics" type (second harmonic generation, frequency conversion, parametric effects) and electro-optical type (Pockels effect).

Prior Art

During the past ten years the investigation of crystal structures exhibiting quadratic nonlinear effects which are augumented when compared with materials such as potassium dihydrogenphosophate (Okada et al., Jap. J. Appl. Phys. 16, 55, 1977) as well as a wide transparency range extending from the visible to the near infrared, has centered on organic molecules such as those listed, for example, in the book published by D. S. Chemia and J. Zyss, Academic Press (1987) "Nonlinear Optical Properties of Organic Molecules and Crystals".

These organic crystals may be in the form of a set of molecular dipoles forming a polar stacking in the crystal lattice.

The highest nonlinear coefficient is oriented along these dipoles. Among the crystal structures of this type there may be mentioned:

POM (3-methyl-4-nitropyridine 1-oxide) (J. Zyss, D. S. Chemia and J. F. Nicoud, J. chem. Phys. 74, 4800, (1981)), NPP (N-(4-nitrophenyl)-L-prolinol) (J. Zyss, J. F. Nicoud and A. Coquillay, J. chem. Phys. 81, 4160 (1984)), NPAN (N-(4-nitrophenyl)-N-dimethylaminoacetonitrile) (P. Vidakovic, M. Coquillay and A. Salin, J. Opt. Soc. Am. B4, 998, (1987)).

These crystals exhibit an exceptionally high nonlinearity (for example $d_{21}$ of the order of 50 pm/V in the case of NPP), but at the cost of a transparency which is limited towards the blue part of the spectrum. Furthermore, the cohesion and the air-stability of such crystals under usual conditions of application may present disadvantages in the case of some of them; this is particularly the case with POM, which must be immersed in a protective liquid and furthermore exhibits a marked tendency to sublimation.

It has recently been proposed by R. Masse and J. Zyss (Molecular Engineering 1, 141, 1991) to encapsulate nonlinear organic molecules in a "framework" array consisting of inorganic anions associated with each other by a single or multiple hydrogen bond, with inorganic anions. The polyanions proposed are of arsenate $(H_2AsO_4^-)_n$, sulfate $(HSO_4^-)_n$ or phosphate $(H_2PO_4^-)_n$ type. A particularly advantageous cystal has been identified in this class: 2-amino-5-nitropyridiniumdihydrogen monophosphate (2A5NPDP).

This crystal structure, of mm2 point symmetry exhibits an inclination of the order of 36° of the transition dipoles of the organic unit in relation to the crystal polar axis, and this favors the coefficient $d_{31}$ (of the order of 10 pm/V) and the parametric effects requiring phase tuning by birefringence (second harmonic generation, parametric amplification).

It is nevertheless desirable to find other crystal structures where a coefficient $d_{ii}$ (with i=1, 2 or 3) would be preferentially optimized by the most perfect possible alignment of the molecules in the lattice along a crystallographic direction i, resembling the crystals of MNA (2-methyl-4-nitroaniline) as described by G. Lipscomb, A. Garito and R. Narang (J. chem. Phys. 75, 1509, (1981)) or crystals of DMACB (4,4'-dimethylaminocyanobiphenyl) as described by J. Zyss, I. Ledoux, M. Bertault, and E. Toupet (Chem. Phys. 150, 125, (1991)).

It is recalled that the coefficients $d_{21}$ and $d_{22}$ refer to the coefficients of the quadratic nonlinear susceptibility tensor, the axis 2 being the axis of linear symmetry in the crystallographic group $P2_1$ (contrast rotation).

Reference should also be made, furthermore, to G. R. Meredith (ACS Symposium Series, 233, 27–56 (1983)), who has developed organic salts for quadratic nonlinear optics, in which the cations exhibiting an intramolecular charge transfer character are used in combination with chiral or achiral organic or inorganic anions. The anions employed in this reference are independent units which are not organized into a polyanionic structure, and the mechanical cohesion of such structures is still not sufficient.

SUMMARY OF THE INVENTION

In the light of the prior art set out above, one of the objectives of the invention is to propose new noncentrosymmetric crystal structures exhibiting quadratic nonlinear effects.

A second objective of the invention is to propose crystal structures exhibiting quadratic nonlinear effects which are increased when compared with those of the prior art.

Another objective of the present invention is to propose crystal structure exhibiting quadratic nonlinear effects and an excellent cohesion of the organic molecular units in the crystal.

Further objectives of the invention will appear on reading the description which is to follow.

According to the present invention the noncentrosymmetric crystal structure consists of an, optionally substituted, 2-amino-5-nitropyridinium halide.

The substituents of the 2-amino-5-nitropyridinium cations are those which do not significantly alter the favorable orientation of the polarizable organic unit in the crystal lattice.

The halide is preferably a chloride ion, a bromide ion or a fluoride ion.

According to a preferred alternative form the crystal structure is such that the cation corresponds to the following formula:

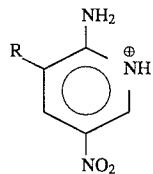

in which:

R denotes a hydrogen atom, a methyl or ethyl radical or a hydroxyl radical.

The cation is also preferably 2-amino-5-nitropyridinium.

Without being bound in any way whatsoever to a scientific theory, the Applicant nevertheless believes that these structures have a specific cohesion due to hydrogen bonds which are short and therefore highly energetic, permitting the aggregation of the cations around the halide anions. Bonding of this type gives the crystal structure according to the invention stability, transparency and ease of growth.

Also preferably, the crystal structure according to the invention is a monocrystal.

The invention also relates to a process for the preparation of the crystal structures as just described in the above description, in which one mole of an optionally substituted 2-amino-5-nitropyridine is mixed with at least one mole of a hydrogen halide in a suitable solvent, the mixture is caused to crystallize and the crystal structures are recovered.

The suitable solvent is especially water or an acetone/water mixture.

One mole of an optionally substituted 2-amino-5-nitropyridine will be preferably mixed with between 0.3 and 2 moles of a hydrogen halide.

The crystallization is performed by slow evaporation of the solvent. A method which is well known to a person skilled in the art is therefore involved.

Advantageously, in a solution which is saturated in rotation with an anion-cation mixture, a crystal seed of a crystal structure such as described above will be present. Slow evaporation results in the crystallization which is sought, at constant temperature (especially ambient temperature). This temperature can also be gradually lowered.

The monocrystals have the required properties, that is to say a polar crystal structure compatible both with the requirements of nonlinear optics (quadratic effects) and of ferroelectricity, a nonlinear response and a satisfactory transparency-efficiency compromise.

Finally, the invention relates to a device with an electro-optical effect comprising a crystal structure as described above. These devices generate a second harmonic or more generally a sum or difference of frequencies. The applications which stem from these advantageous properties are numerous, both as bulk crystal and as a guiding structure, such as, phase modulation of an optical carrier amplitude modulation directive coupler, electro-optical crossover and more generally electro-optical switching point, electro-optical sampling, electronic logic' electro-optical triggering of lasers ("Q-Switch") without prejudice to applications requiring a phase tuning using birefringence, such as:

second harmonic generation, frequency conversions parametric amplification, emission and oscillation.

By way of example, a laser cavity with electrooptical triggering, provided with a crystal structure according to the invention is described below.

In such a device a crystal structure according to the invention is introduced into the cavity of a laser (for example a YAG laser emitting at 1.06 or 1.34 m and more generally any laser emitting in the crystal transparency range of 0.45 to 1.7 m) in a configuration of the Pockels cell type. The interplay of polarizations and reflections results in a blocking of the emission when the crystal is under tension. In the absence of tension the crystal becomes transmitting again and the cavity can emit. A general scheme of the principle is shown, for example in R. W. Hellwarth "Q Modulation of lasers" in Lasers, vol. 1, A. K. Levine ed. (New York, Marcel Dekker, 1996) p. 253.

BRIEF DESCRIPTION OF THE DRAWINGS

The invention is now illustrated by the embodiments given by way of guidance below and by FIGS. 1 and 2, appended.

Figure 1:
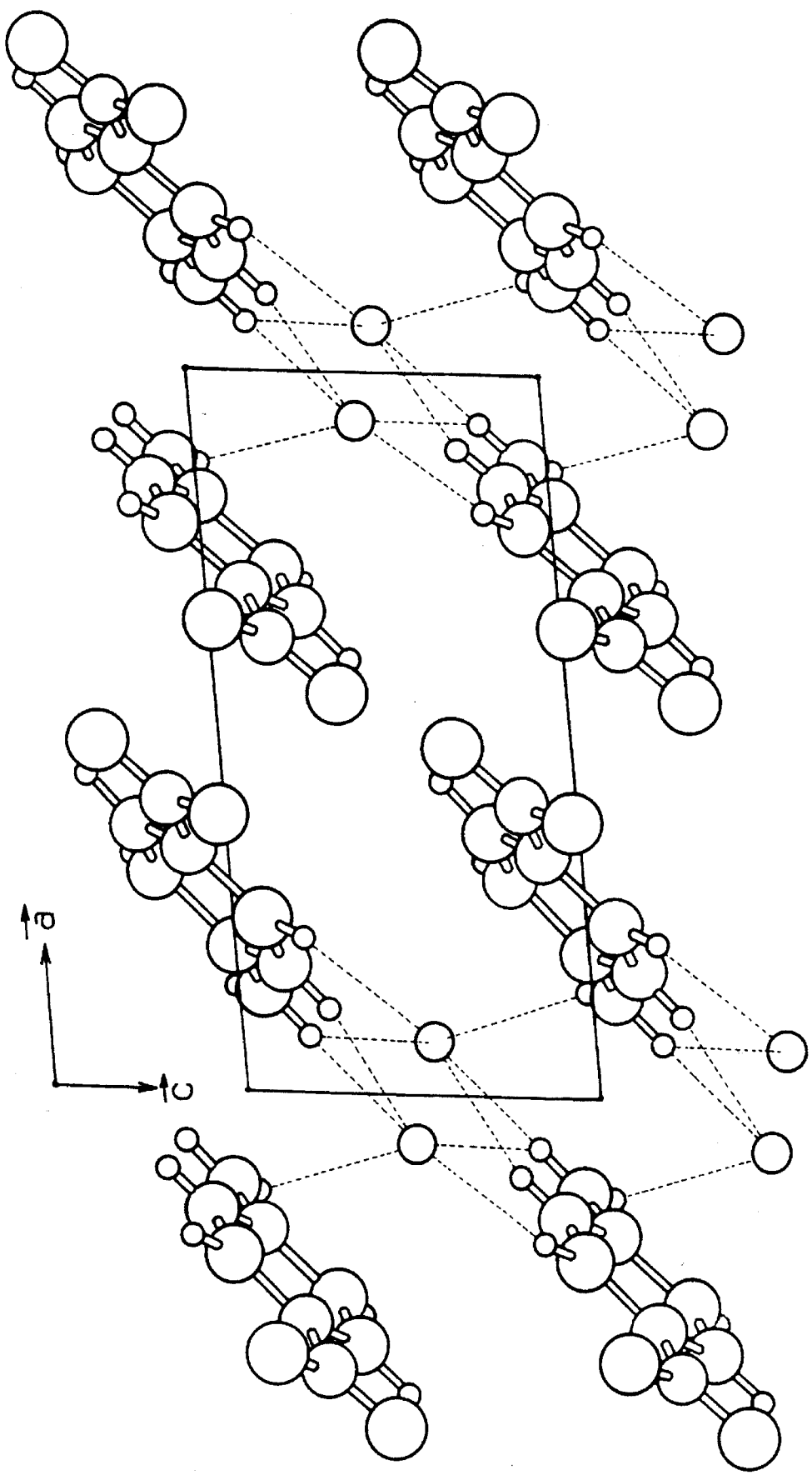
FIG. 1 shows the crystal lattice of the 2-amino-5-nitropyridinium chloride crystal projected in the $[\vec{a}, \vec{c}]$ crystallographic plane.
Figure 2:
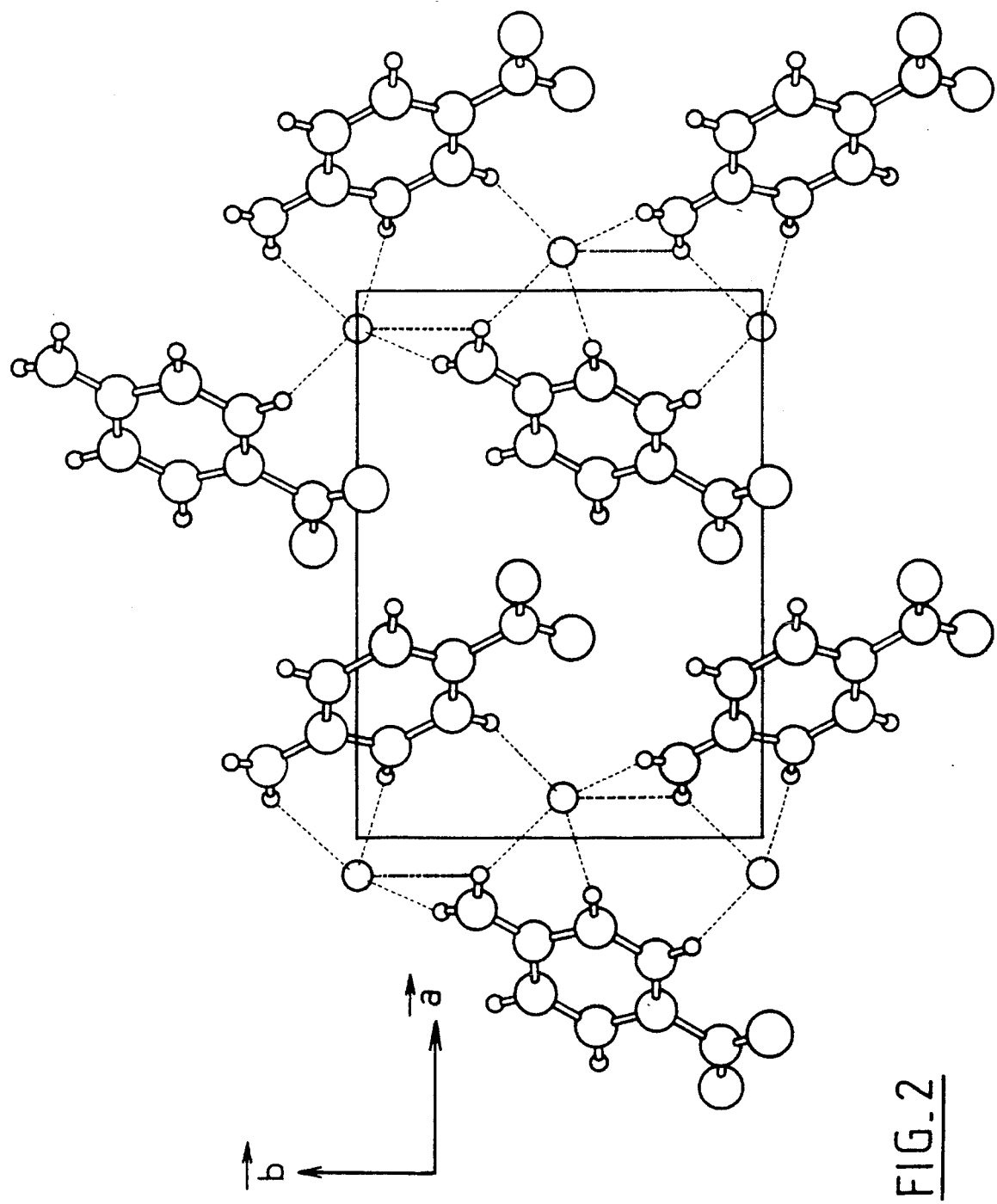
FIG. 2 shows the same crystal projected in the $[\vec{a}, \vec{b}]$ plane.

The noncentrosymmetric structure of the crystals according to the invention can be seen on reading these figures, where a layer of anions separating the organic dipoles can be noted, which are oriented in patterns of herringbone type in a single polar direction ($P2_1$ structure).

EXAMPLE 1

One mole of 2-amino-5-nitropyridine (2A5NP) is dissolved completely in the minimum volume of acetone at ambient temperature. 30 cc of a molar solution of hydrochloric or hydrobromic acid are added. The solutions obtained are slowly evaporated at ambient temperature and easily yield transparent crystals 4 mm×4 mm×4 mm in size. The reaction can also be performed in water at 40° C.: 0.8 mole of 2A5NP will then be dissolved per one mole of hydrochloric or hydrobromic acid. Raising the temperature makes it easier to dissolve the 2-amino-5-nitropyridine nitropyridine in the acetone-water mixture.

The chemical reactions are written:

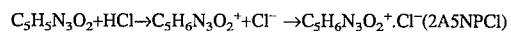

$C_5H_5N_3O_2 + HCl \rightarrow C_5H_6N_3O_2^+ + Cl^- \rightarrow C_5H_6N_3O_2^+ \cdot Cl^- (2A5NPCl)$

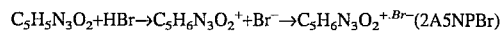

$C_5H_5N_3O_2 + HBr \rightarrow C_5H_6N_3O_2^+ + Br^- \rightarrow C_5H_6N_3O_2^{+,Br^-} (2A5NPBr)$ Investigation of the crystal structures has made it possible to determine unambiguously the chemical formulae and the isomorphology of the two compounds. The active phases are perfectly characterized:

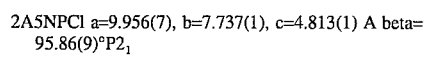

2A5NPCl a=9.956(7), b=7.737(1), c=4.813(1) A beta= 95.86(9)° $P2_1$

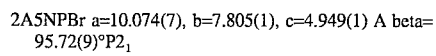

2A5NPBr a=10.074(7), b=7.805(1), c=4.949(1) A beta= 95.72(9)° $P2_1$

EXAMPLE 2: crystal growth

Evaporation of solutions containing one mole of 2A5NP per one mole of HCl (or HBr) in air at ambient temperature produces beautiful crystals of 2-amino-5-nitropyridinium chloride or bromide, both of which have the same morphology ($P2_1$ symmetry). Sturdy crystals of 7 mm×7 mm×5 mm, or even of 10 mm×6 mm×5 mm in the case of the chlorides, have been easily obtained.

These crystals have thermal and mechanical properties equivalent to those of 2A5NPDP.

Furthermore, according to the tests on powder for second harmonic generation (illumination with an Nd:YAG laser, $\lambda=1.06$ μm) their efficiency is closely related to that of POM and of NPP.

What is claimed is:

1. A noncentrosymmetric crystal structure comsisting of a substituted 2-amino-5-nitropyridinium halide of formula

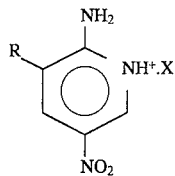

wherein R is selected from the group consisting of a hydrogen atom, a methyl radical, an ethyl radical, or a hydroxyl radical, and wherein X is a halide ion.

2. The noncentrosymmetric crystal structure of claim 1, wherein X is selected from the group consisting of a chloride, bromide, or fluoride ion.

3. The noncentrosymmetric crystal structure of claim 1, wherein said noncentrosymmetric crystal structure is a monocrystal.

* * * * *

UNITED STATES PATENT AND TRADEMARK OFFICE
CERTIFICATE OF CORRECTION

PATENT NO. : 5,514,807
DATED : May 7, 1996
INVENTOR(S) : Pecaut et al.

It is certified that errors appear in the above-identified patent and that said Letters Patent is hereby corrected as shown below:

On the title page, item
 [75] Inventors, please delete " Masses " and insert -- Masse --.

In column 1 at line 66-67, please delete " 2-amino-5-nitropyridiniumdihydrogen" and insert -- 2-amino-5-nitropyridinium dihydrogen --.

In column 4 at line 45, please delete " .Br- " and insert -- .Br- --.

In column 5 at line 6, please delete " comsisting " and insert -- consisting --.

Signed and Sealed this

Seventeenth Day of September, 1996

Attest:

BRUCE LEHMAN

*Attesting Officer*  *Commissioner of Patents and Trademarks*